United States Patent
Im

(10) Patent No.: US 9,695,210 B2
(45) Date of Patent: Jul. 4, 2017

(54) C1-PHOSTPHONATE ANALOGUE OF UDP-GLCNAC FOR INHIBITION OF O-GLCNAC TRANSFERASE

(71) Applicant: SOONCHUNHYANG UNIVERSITY INDUSTRY ACADEMY COOPERATION FOUNDATION, Chungcheongnam-do (KR)

(72) Inventor: Jungkyun Im, Chungcheongnam-do (KR)

(73) Assignee: SOONCHUNHYANG UNIVERSITY INDUSTRY ACADEMY COOPERATION FOUNDATION, Chungcheongnam-Do (KR)

( * ) Notice: Subject to any disclaimer, the term of this patent is extended or adjusted under 35 U.S.C. 154(b) by 0 days.

(21) Appl. No.: 14/969,136

(22) Filed: Dec. 15, 2015

(65) Prior Publication Data

US 2017/0022243 A1    Jan. 26, 2017

(30) Foreign Application Priority Data

Jul. 20, 2015    (KR) .................. 10-2015-0102137

(51) Int. Cl.
| | | |
|---|---|---|
| *C07H 19/00* | (2006.01) | |
| *C07H 19/10* | (2006.01) | |
| *C07H 1/02* | (2006.01) | |
| *C07H 19/06* | (2006.01) | |
| *C07H 1/04* | (2006.01) | |
| *C07H 19/067* | (2006.01) | |

(52) U.S. Cl.
CPC .............. *C07H 19/10* (2013.01); *C07H 1/02* (2013.01); *C07H 1/04* (2013.01); *C07H 19/06* (2013.01); *C07H 19/067* (2013.01)

(58) Field of Classification Search
None
See application file for complete search history.

(56) References Cited

FOREIGN PATENT DOCUMENTS

KR    20140041406    4/2014

OTHER PUBLICATIONS

Bhattacharya et al. Tetrahedron Letters (2001), vol. 42, pp. 5393-5395.*
"Representative." Oxforddictionaries.com. Oxford Dictionary, n.d. Web. Jan. 4, 2017.*
Schimpl et al., "Synergy of Peptide and Sugar in O-GlcNacase Substrate Recognition", Feb. 2012, Chemistry & Biology 19, 173-178, UK.
Hart et al., "Cycling of O-linked . . . ", Apr. 2007, Nature Publishing Group, vol. 446, 1017-1022, Maryland, USA.
Hu et al., "Site-specific interplay . . . ", Apr. 2010, Epsev9er B.V., 584, 2526-2538, Maryland, USA.
Li et al., "Glycosylation of the Nuclear Pore", Traffic 2014, 15, 347-361.
Zhang et al., "O-GlcNAc Modification . . . " Cell Press, Dec. 2003, vol. 115, 715-725.
Donovan et al., "OglcNAc Modification of Transcription . . . " Invest. Ophthalmol. Vis. Sci. Dec. 2014, vol. 55, No. 12, 7862-7872.
Wells et al., "Glycosylation of Nucleocytoplasmic Protieins . . . " Science, Mar. 2001, vol. 291, 2376-2378.
Konopka, "N-Acetylglucosamine Functions in Cell Signaling", Scientifica, Oct. 1-15, 2012, USA.
Rexach et al., "Chemical approaches to understanding . . . " Nature Chemical Biology, Jan. 2008, vol. 4, No. 2 97-106.

* cited by examiner

*Primary Examiner* — Patrick Lewis
(74) *Attorney, Agent, or Firm* — IPLA P.A.; James E. Bame

(57) ABSTRACT

A novel C1-phosphate log of uridine-5'-diphosphate (UDP)-GlcNAc as an effective OGT (O-linked N-acetylglucosamine (O-GlcNAc) transferase) inhibitor, and a preparation method for the same provides a compound having an OGT inhibitory effect that can be used as a useful tool in the studies on various vital phenomena in association with the protein modification by O-GlcNAc within cells and furthermore as a candidate substance in the treatment or research of diseases related to the protein modification by O-GlcNAc, such as cancers, diabetes, or degenerative neurological diseases.

8 Claims, 1 Drawing Sheet

C1-PHOSTPHONATE ANALOGUE OF UDP-GLCNAC FOR INHIBITION OF O-GLCNAC TRANSFERASE

BACKGROUND

The present invention relates to a novel C1-phosphate analogue of uridine-5'-diphosphate (UDP)-GlcNAc effective as an OGT (O-linked N-acetylglucosamine (O-GlcNAc) transferase) inhibitor, and a preparation method thereof.

As for the post-transcriptional modification of proteins by O-GlcNAc, the hydroxyl moiety of serine or threonine residues at nuclear or cytosolic proteins in eukaryotic cells is modified into one O-linked β-N-acetylglucosamine. The modification occurs in all kinds of eukaryotic cells from yeast to human.

Several scores of O-GlcNAc-modified proteins have been identified for twenty years after the discovery of O-GlcNAc, proving that O-GlcNAc has an important role in the cell regulation mechanisms, including transcription, translation, cell signaling, protein stability, nuclear localization, and so forth.

Beginning from nuclear pore proteins, a variety of proteins modified by O-GlcNAc have also been identified, including cytoskeletal proteins and their related regulatory proteins, viral proteins, nuclear proteins, tumor suppressor, nuclear oncogene proteins, catalytic subunits of RNA polymerase II, and many transcription factors. There is no interrelationship between these O-GlcNAc-modified proteins, but one thing in common is that they are all phosphoproteins. Most of the O-GlcNAc-modified proteins are known to assemble into highly controlled multimeric forms, which are, in many cases, regulated by post-translational modification.

It is discovered that O-GlcNAc metabolism/modification is closely related with various human diseases, such as diabetes, degenerative brain diseases, neurogenic brain diseases, cancers, etc.

The enzyme that enacts the transfer of GlcNAc is O-GlcNAc transferase (OGT), and the donor substrate is uridine-5'-diphosphate (UDP)-GlcNAc. For more studies on the biological functions of O-GlcNAc and the molecular-scale structure of OGT, it is necessary to search for substances suitable for effective inhibition of OGT. However, there is still no well known substance that displays an OGT inhibitory effect.

It is therefore necessary to develop a novel UDP-GlcNAc analogue as a novel inhibitor for O-GlcNAc transferase (OGT).

RELATED APPLICATIONS

Patent Document (Patent Document 1) KR 10-2014-0041406 A

Non-Patent Documents (Non-Patent Document 1) M. Schimpl, V. S. Borodkin, L. J. Gray, D. M. F. van Aalten, Chem. Biol. 2012, 19, 173.
(Non-Patent Document 2) G. W. Hart, M. P. Housley, C. Slawson, Nature 2007, 446, 1017.
(Non-Patent Document 3) P. Hu, S. Shimoji, G. W. Hart, FEBS Lett. 2010, 584, 2526.
(Non-Patent Document 4) B. Li, J. J. Kohler, Traffic 2014, 15, 347.
(Non-Patent Document 5) F. Zhang, K. Su, X. Yang, D. B. Bowe, A. J. Paterson, J. E. Kudlow, Cell 2003, 115, 715.
(Non-Patent Document 6) K. Donovan, O. Alekseev, X. Qi, W. Cho, J. Azizkhan-Clifford, Invest. Ophthalmol. Vis. Sci. 2014, 55, 7862.
(Non-Patent Document 7) L. Wells, K. Vosseller, G. W. Hart, Science 2001, 291, 2376.
(Non-Patent Document 8) J. B. Konopka, Scientifica 2012, 2012, 1.
(Non-Patent Document 9) J. E. Rexach, P. M. Clark, L. C. Hsieh-Wilson, Nat. Chem. Biol. 2008, 4, 97.

SUMMARY OF THE INVENTION

The present invention is to provide a novel OGT (O-Linked N-Acetylglucosamine Transferase; O-GlcNAc transferase) inhibitor that offers help in the treatment or research of cancers, diabetes or degenerative neurological disorders such as Alzheimer's disease.

The present invention provides a compound represented by the following chemical formula 1:

[Chemical Formula 1]

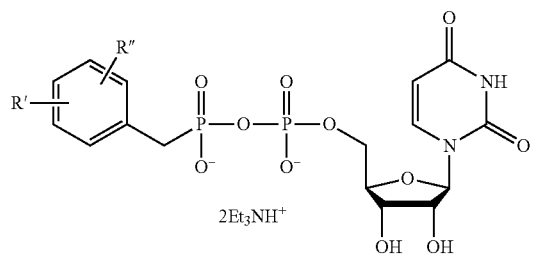

In the chemical formula 1, R' is selected from the group consisting of —($C_1$-$C_{10}$-alkyl)-OH, —($C_1$-$C_{10}$-alkyl)-O—($C_1$-$C_6$-alkyl), —($C_1$-$C_{10}$-alkyl)-O—($C_1$-$C_6$-alkenyl), —($C_1$-$C_{10}$-alkyl)-O—($C_1$-$C_6$-alkynyl), —($C_1$-$C_6$-alkyl)-C(=O)—($C_1$-$C_6$-alkyl), —($C_1$-$C_6$-alkyl)-C(=O)—($C_1$-$C_6$-alkenyl), —($C_1$-$C_6$-alkyl)-C(=O)—($C_1$-$C_6$-alkynyl), and —($C_1$-$C_6$-alkyl)-C(=O)—O—($C_1$-$C_6$-alkyl);

R" is $NH_2$ or NHR; and

R is selected from the group consisting of —C(=O)—($C_1$-$C_{10}$-alkyl), —C(=O)—($C_1$-$C_{10}$-alkenyl), —C(=O)—($C_1$-$C_{10}$-alkynyl), —C(=O)—O—($C_1$-$C_{10}$-alkyl), —C(=O)—O—($C_1$-$C_{10}$-alkenyl), and —C(=O)—O—($C_1$-$C_{10}$-alkynyl).

More specifically, in accordance with an embodiment of the present invention, the compound of the chemical formula 1 is represented by any one of the following chemical formulas 1-1 to 1-9:

<Chemical Formula 1-1>

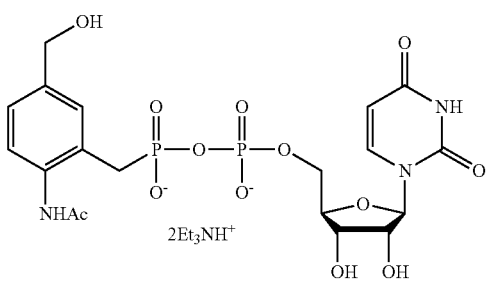

<Chemical Formula 1-2>

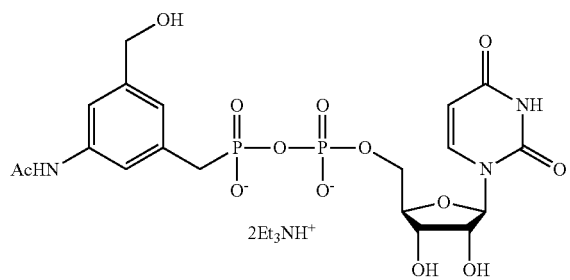

<Chemical Formula 1-3>

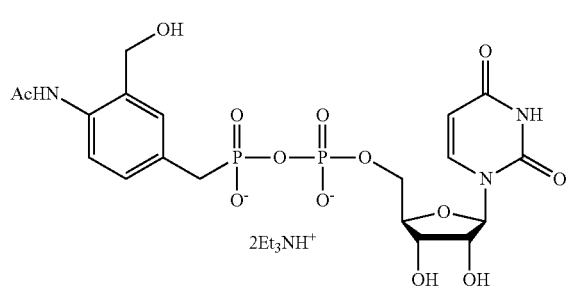

<Chemical Formula 1-4>

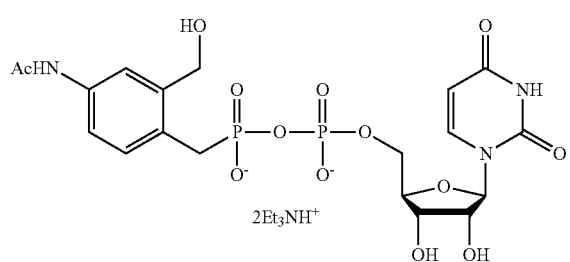

<Chemical Formula 1-5>

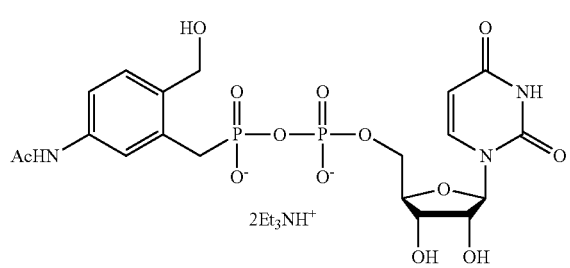

<Chemical Formula 1-6>

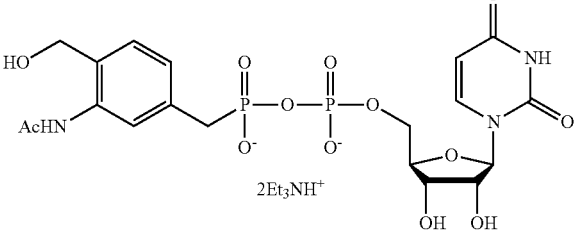

<Chemical Formula 1-7>

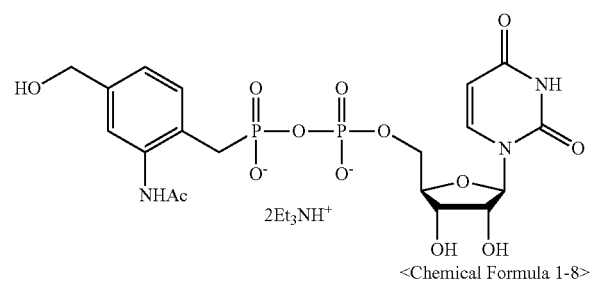

<Chemical Formula 1-8>

<Chemical Formula 1-9>

In another aspect of the present invention, there is provided a method for preparing the compound of the chemical formula 1. The method for preparing the compound of the chemical formula 1 includes: (1) preparing a compound represented by the following chemical formula A; (2) preparing a compound represented by the following chemical formula B from the compound of the chemical formula A; and (3) synthesizing the compound represented by the chemical formula 1 from the compound of the chemical formula B,

[Chemical Formula A]

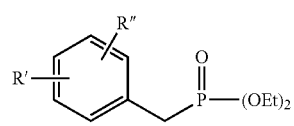

[Chemical Formula B]

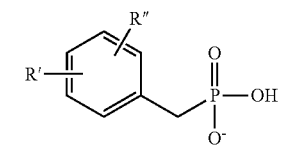

The C1-phosphate analogue of uridine-5'-diphosphate (UDP)-GlcNAc as provided by the present invention inhibits OGT (O-linked N-acetylglucosamine (O-GlcNAc) transferase), so it can be used as a useful tool in the studies on various vital phenomena in association with the protein modification by O-GlcNAc within cells, and furthermore used as a candidate substance in the treatment or mechanism research of diseases related to the protein modification by O-GlcNAc, such as cancers, diabetes, or degenerative neurological diseases.

DETAILED DESCRIPTION OF THE INVENTION

Figure 1A:
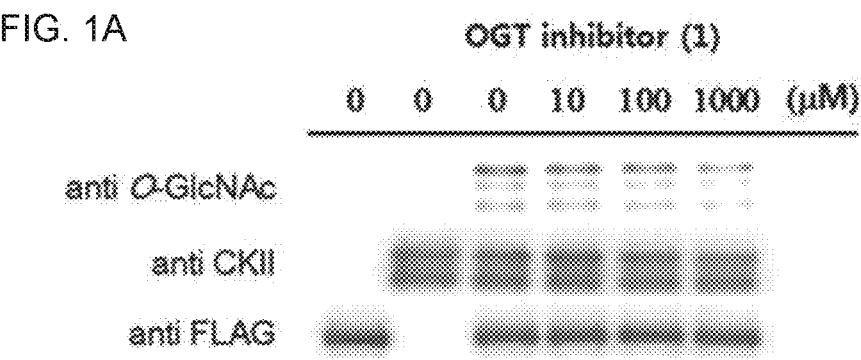
FIGS. 1A and 1B shows the results of a test on the inhibitory activity of analogue 1 on OGT.

Hereinafter, the present invention will be described in further detail with reference to examples. In the following description of the present invention, a detailed description of known functions and configurations incorporated herein will be omitted when it may make the subject matter of the present invention rather unclear.

In the following description, reference will be made to the preparation examples of a compound in which R' and R" are $CH_2OH$ and NHAc, respectively, in association with a synthesis example of the UDP-GlcNAc analogue represented by the chemical formula 1 according to the present invention, which examples are not intended to limit the scope of the present invention.

[Example] Synthesis

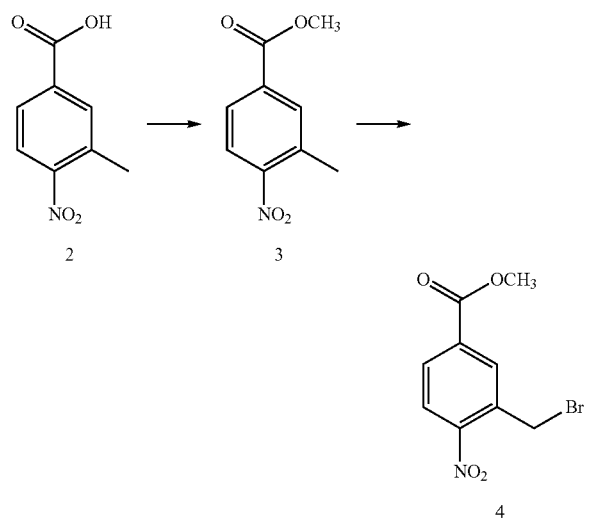

Preparation Example 1: Preparation of 3-methyl-4-nitrobenzoic acid methylester (3)

Concentrated sulfuric acid ($H_2SO_4$, 97%, 2.66 ml, 48.41 mmol) is added to a solution containing the compound 2 (3-methyl-4-nitrobenzoic acid, 4.53 g, 29.98 mmol) in methanol (MeOH) (25 ml) at the room temperature. After an overnight reflux under agitation, the cloudy reactant mixture becomes clear and then cooled down at the room temperature into a suspension. The precipitate is filled out and washed with cold water. A recrystallization with methanol and a filtration and drying process yields the compound 3 (1.67 g, 37%) as yellowish solid crystals.

$R_f$: 0.5 (EtOAc:Hex=1:5); m.p. 79.5-80.0° C.; IR (film, $cm^{-1}$) 3118 and 3046 (=C—H), 2959 (—C—H), 1732 (C=O), 1585 (Ar), 1520 (N=O), 1429 (Ar), 1344 (N=O); $^1$H NMR (in $CDCl_3$), 2.63 (s, 3H, $CCH_3$), 3.96 (s, 3H, $OCH_3$), 7.98 (s, 2H), 8.03 (s, 1H) [aromatic protons]; $^{13}$C NMR (in $CDCl_3$) 20.30 ($C\underline{C}H_3$), 52.94 ($OCH_3$), 124.80, 128.28, 133.70, 133.96, 134.23, 152.10 (aromatic carbons), 165.56 (C=O); HR-FABMS [M+H]$^+$ calcd for $C_9H_{10}NO_4$ m/z 196.0610, found 196.0608.

Preparation Example 2: Preparation of 3-bromomethyl-4-nitrobenzoic acid methylester (4)

Benzoyl peroxide (200 mg, 0.83 mmol) and n-bromosuccinimide (1.98 g, 11.14 mmol) are added to a solution containing the compound 3 (1.33 g, 7.43 mmol) dissolved in anhydrous $CCl_4$ (34 ml) at the room temperature. The reactant mixture is subjected to a 16-hour reflux under agitation and then cooled down to the room temperature. The mixture is filtered and washed with hexane. The filtrate is concentrated under vacuum, and the residue is purified by column chromatography to yield a compound 4 (0.98 g, 48%) as a white solid and 3-dibromomethyl-4-nitrobenzoic acid methylester (0.89 g, 34%) as a white solid by-product.

$R_f$: 0.4 (EtOAc:Hex=1:10); m.p. 117.0-117.5° C.; IR (film, $cm^{-1}$) 3124 and 3053 (=C—H), 3002 and 2952 (—C—H), 1722 (C=O), 1586 (Ar), 1529 (N=O), 1442 (Ar), 1356 (N=O), 1277 ($CH_2$—Br, bending), 624 (C—Br); $^1$H NMR (in $CDCl_3$) 3.99 (s, 3H, $OCH_3$), 4.83 (s, 2H, $CH_2Br$), 8.06 (d, 1H, J=8.43 Hz), 8.13 (dd, 1H, J=8.49 and 1.77 Hz), 8.24 (d, 1H, J=1.59 Hz) [aromatic protons]; $^{13}$C NMR (in $CDCl_3$) 28.09 (CBr), 53.17 ($OCH_3$), 125.80, 130.83, 133.28, 133.95, 134.80, 150.72 (aromatic carbons), 164.85 (C=O); HR-FABMS [M+H]$^+$ calcd for $C_9H_9BrNO_4$ m/z 273.9715, found 273.9711.

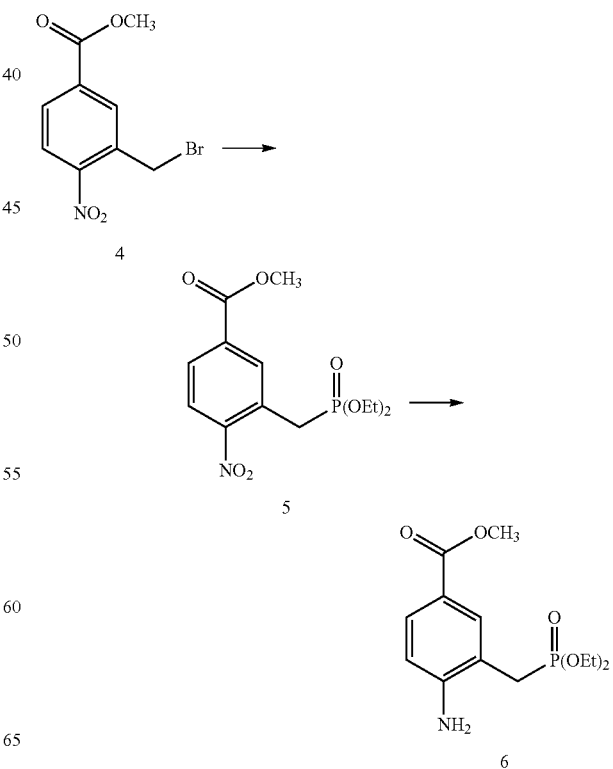

Preparation Example 3: Preparation of 3-(diethoxy-phosphorylmethyl)-4-nitrobenzoic acid methylester (5)

2.40 ml (13.72 mmol) of triethylphosphite is added to a solution containing the compound 4 (0.85 g, 3.11 mmol) in toluene (40 ml) at the room temperature. The reactant mixture is stirred at 115° C. for 28 hours and cooled down to the room temperature. The resultant solution is concentrated under vacuum and distilled at 70° C. The product is purified by column chromatography to yield a compound 5 (0.77 g, 75.10%) as an yellowish oil.

$R_f$: 0.5 (EtOAc:Hex=2:1); IR (film, cm$^{-1}$) 3111 and 3044 (=C—H), 2956 and 2908 (—C—H), 1729 (C=O), 1586 (Ar), 1533 (N=O), 1438 (Ar), 1357 (N=O), 1271 (P=O), 1024 (P-OEt); $^1$H NMR (in CDCl$_3$) 1.25 (t, 6H, J=7.08 Hz, CH$_2$CH$_3$), 3.72 (d, 2H, J=22.56 Hz, CH$_2$P), 3.97 (s, 3H, OCH$_3$), 3.99-4.10 (m, 4H, OCH$_2$), 7.98 (d, 1H, J=8.49 Hz), 8.06 (ddd, 1H, J=8.49 and 1.98 Hz), 8.13 (dd, 1H, J=2.04 Hz) [aromatic protons]; $^{31}$P NMR (in CDCl$_3$) 24.38; HR-FABMS [M+H]$^+$ calcd for C$_{13}$H$_{19}$NO$_7$P m/z 332.0899, found 332.0896.

Preparation Example 4: Preparation of 4-amino-3-(diethoxy-phosphorylmethyl)-benzoic acid methylester (6)

A solution containing the compound 5 (0.74 mg, 2.24 mmol) and Pd/C 10% (200 mg) in methanol (26 ml) is stirred in the hydrogen atmosphere (50 psi) for 4 hours. The reactant mixture is filtered through a cellite pad and washed with methanol. A distillation under reduced pressure is carried out to yield an amino compound 6 (0.60 mg, 89%) as a yellowish sticky solid.

$R_f$: 0.3 (EtOAc:Hex=2:1); IR (film, cm$^{-1}$) 3356 and 3242 (N—H), 2983, 2952 and 2928 (—C—H), 1708 (C=O), 1606 (N—H, bending), 1577 and 1430 (Ar), 1277 (P=O), 1025 (P-OEt); $^1$H NMR (in MeOD) 1.29 (t, 6H, J=7.04 Hz, CH$_2$CH$_3$), 3.22 (d, 2H, J=21.01 Hz, CH$_2$P), 3.85 (s, 3H, OCH$_3$), 4.04-4.13 (m, 4H, OCH$_2$), 6.77 (d, 1H, J=8.48 Hz), 7.70 (ddd, 1H, J=8.47 and 2.04 Hz), 7.80 (dd, 1H, J=2.37 Hz) [aromatic protons]; $^{13}$C NMR (in MeOD) 16.76 (d, J=5.93 Hz, CH$_2$CH$_3$), 29.71 (d, J=138.83 Hz, CH$_2$P), 64.01 (d, J=6.98 Hz, OCH$_2$), 116.09 (d, J=9.38 Hz), 116.29 (d, J=2.25 Hz), 119.68 (d, J=2.78 Hz), 131.25 (d, J=2.85 Hz), 134.94 (d, J=6.45 Hz), 153.12 (d, J=4.80 Hz) [aromatic carbons], 169.04 (C=O); $^{31}$P NMR (in MeOD) 28.64; HR-FABMS [M+H]$^+$ calcd for C$_{13}$H$_{21}$NO$_5$P m/z 302.1157, found 302.1158.

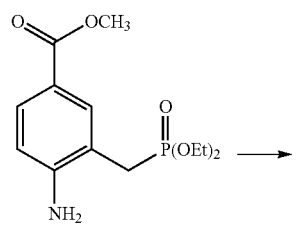

6

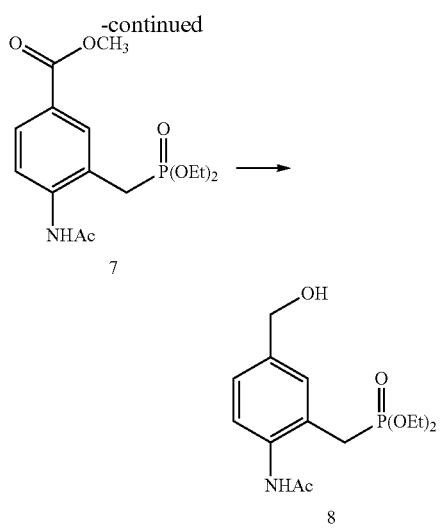

7

8

Preparation Example 5: Preparation of 4-acetylamino-3-(diethoxy-phosphorylmethyl)-benzoic acid methyl ester (7)

The compound 6 (0.45 mg, 1.50 mmol) is dissolved in dried pyridine (10 ml), and acetic anhydride (0.60 ml, 6.39 mmol) is added to the resultant solution at the room temperature. After an overnight agitation, the reactant mixture is diluted with EtOAc and neutralized with HCl (1N). The organic layer is washed with HCl (1N) twice and then again with aqueous NaHCO$_3$ and saline water successively. The organic layer is dried with MgSO$_4$ and then subjected to filtration and concentration to yield a product, which is purified by column chromatography to obtain a compound 7 (0.37 mg, 73%) as a colorless oil.

$R_f$: 0.5 (EtOAc:Hex=2:1); IR (film, cm$^{-1}$) 3251 (N—H), 3109 (=C—H), 2982, 2953 and 2924 (—C—H), 1716 (C=O, ester), 1668 (C=O, amide), 1590 and 1436 (Ar), 1285 (P=O), 1024 (P-OEt); $^1$H NMR (in CDCl$_3$) 1.25 (t, 6H, J=7.02 Hz, CH$_2$CH$_3$), 2.23 (s, 3H, C=OCH$_3$), 3.19 (d, 2H, J=21.12 Hz, CH$_2$P), 3.90 (s, 3H, OCH$_3$), 3.95-4.08 (m, 4H, OCH$_2$), 7.86 (s, 1H), 7.90 (d, 1H, J=8.52 Hz), 8.01 (d, 1H, J=8.55 Hz) [aromatic protons]; $^{31}$P NMR (in CDCl$_3$) 28.64; HR-FABMS [M+H]$^+$ calcd for C$_{15}$H$_{23}$NO$_6$P m/z 344.1263, found 344.1267.

Preparation Example 6: Preparation of diethyl-(2-acetylamino-5-hydroxymethyl-benzyl)-phosphonate (8)

The compound 7 (0.36 mg, 1.03 mmol) and LiBH$_4$ (4 ml, 2.0 M in THF) are stirred at the room temperature for 3 days. To the reactant mixture is added aqueous NH$_4$Cl dropwise at 0° C. until there is no more bubbles formed. The suspended product is diluted with EtOAc and washed with aqueous NH$_4$Cl and brine. The organic layer is dried with anhydrous MgSO$_4$ and then subjected to filtration and concentration. The concentrated organic layer is purified by column chromatography to yield a compound 8 (0.24 mg, 73%) as a colorless oil.

$R_f$: 0.5 (CH$_2$Cl$_2$:MeOH=10:1); IR (film, cm$^{-1}$) 3297 (O—H, broad), 3120 (=C—H), 2983, 2925 and 2854 (—C—H), 1673 (C=O), 1595 and 1442 (Ar), 1282 (P=O), 1025 (P-OEt); $^1$H NMR (in CDCl$_3$) 1.24 (t, 6H, J=7.03 Hz, CH$_2$CH$_3$), 2.20 (s, 3H, C=OCH$_3$), 3.13 (d, 2H, J=21.15 Hz, CH$_2$P), 3.93-4.08 (m, 4H, OCH$_2$), 4.62 (s, 2H, CH$_2$OH), 7.17 (s, 1H), 7.24 (d, 1H, J=8.20 Hz), 7.73 (d, 1H, J=8.22 Hz) [aromatic protons]; $^{13}$C NMR (in CDCl$_3$) 16.50 (d, J=5.78 Hz, OCH$_2$CH$_3$), 24.33 (C=OCH$_3$), 31.37 (d, J=137.03 Hz, CH$_2$P), 63.13 (d, J=6.98 Hz, OCH$_2$CH$_3$), 64.71 (CH$_2$OH), 123.76 (d, J=9.45 Hz), 125.92 (d, J=3.23 Hz), 126.82 (d, J=3.68 Hz), 129.95 (d, J=7.05 Hz), 126.23 (d, J=5.03 Hz), 138.42 (d, J=2.70 Hz) [aromatic carbons], 169.41 (C=O); $^{31}$P NMR (in CDCl$_3$) 29.14; HR-FABMS [M+H]$^+$ calcd for C$_{14}$H$_{23}$NO$_5$P m/z 316.1314, found 316.1312.

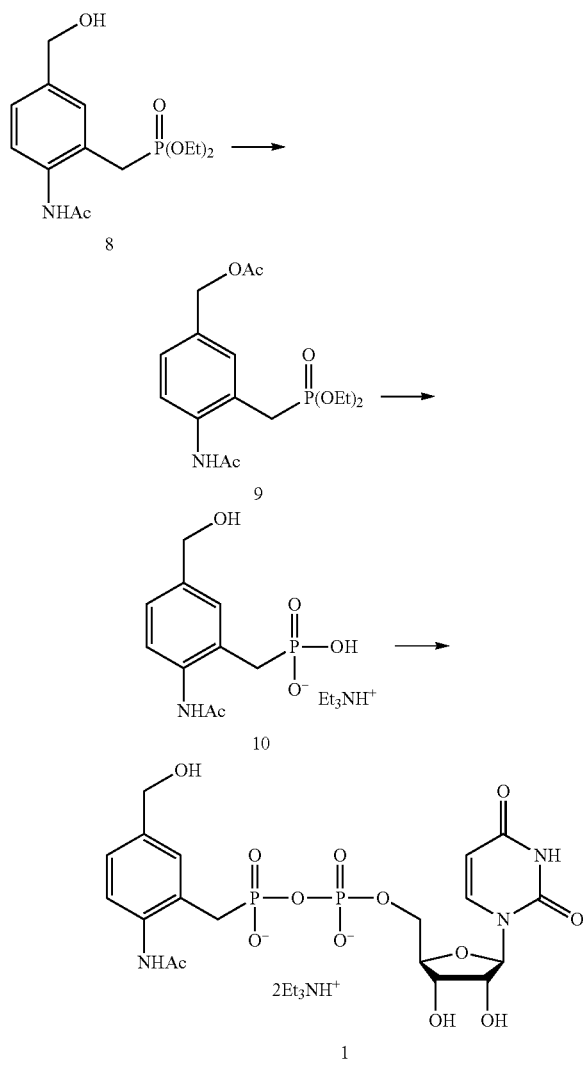

then with aqueous NaHCO$_3$ and brine. The organic layer is dried with anhydrous MgSO$_4$ and then subjected to filtration and concentration. The concentrated organic layer is purified by column chromatography to yield a compound 9 (137 mg, 83%) as a colorless oil.

R$_f$: 0.7 (EtOAc:MeOH=20:1); IR (film, cm$^{-1}$) 3263 (N—H), 3116 (=C—H), 2984 and 2932 (—C—H), 1739 (C=O, ester), 1694 (C=O, amide), 1596 and 1443 (Ar), 1282 (P=O), 1229 (OC—O), 1026 (P-OEt); $^1$H NMR (in CDCl$_3$) 1.24 (t, 6H, J=7.00 Hz, CH$_2$CH$_3$), 2.08 (s, 3H, OC=OCH$_3$), 2.21 (s, 3H, NC=OCH$_3$), 3.14 (d, 2H, J=21.14 Hz, CH$_2$P), 3.97-4.06 (m, 4H, OCH$_2$CH$_3$), 5.05 (s, 2H, CH$_2$OC=O), 7.15 (s, 1H), 7.29 (d, 1H, J=6.70 Hz), 7.80 (d, 1H, J=8.23 Hz) [aromatic protons], 9.54 (s, 1H, NH); $^{13}$C NMR (in CDCl$_3$) 16.44 (d, J=5.85 Hz, CH$_2$CH$_3$), 21.13 (OC=OCH$_3$), 24.36 (NC=OCH$_3$), 31.40 (d, J=137.02 Hz, CH$_2$P), 63.13 (d, J=6.98 Hz, OCH$_2$CH$_3$), 65.81 (CH$_2$OC=O), 123.64 (d, J=9.45 Hz), 125.81 (d, J=2.15 Hz), 128.37 (d, J=3.60 Hz), 131.47 (d, J=7.05 Hz), 133.02 (d, J=2.78 Hz), 137.09 (d, J=5.03 Hz) [aromatic carbons], 169.25 (NC=O), 170.90 (OC=O); $^{31}$P NMR (in CDCl$_3$) 28.94; HR-FABMS [M+H]$^+$ calcd for C$_{16}$H$_{25}$NO$_6$P m/z 358.1420, found 358.1418.

Preparation Example 8: Preparation of (2-acetylamino-5-hydroxymethyl-benzyl)-phosphonate, monotriethylammonium salt (10)

The compound 9 (63.60 mg, 0.18 mmol) is dissolved in CH$_2$Cl$_2$ (1 ml), and bromotrimethylsiliane (1 ml, 7.50 mmol) is added to the resultant solution at the room temperature. The solution is under agitation overnight. The solvent and an excess of the reagent are used for distillation with toluene twice. The residue is dissolved in methanol (2 ml) and then treated with a few drops of water at the room temperature. After a 10-hour agitation, the solution is concentrated with toluene twice, and to the concentrated residue is added a mixed solution of MeOH—H$_2$O-Et$_3$N (2 ml, 7:3:1). The mixture is under agitation overnight and then concentrated. The residue thus obtained is purified with reverse-phase silica gel (TEAA:CH$_3$CN=100:0 to 90:10) to yield a compound 10 (40.50 mg, 63%) as a white sticky solid.

$^1$H NMR (in D$_2$O) 1.16 (t, 9H, J=7.31 Hz, CH$_2$CH$_3$), 2.11 (s, 3H, C=OCH$_3$), 2.92 (d, 2H, J=20.43 Hz, CH$_2$P), 3.08 (q, 6H, J=7.30 Hz, NCH$_2$), 4.51 (s, 2H, OCH$_2$), 7.18 (d, 1H, J=7.96 Hz), 7.23 (s, 1H), 7.29 (d, 1H, J=8.08 Hz) [aromatic protons]; $^{13}$C NMR (in D$_2$O) 7.75 (NCH$_2$CH$_3$), 22.05 (C=OCH$_3$), 31.90 (d, J=126.68 Hz, CH$_2$P), 46.20 (NCH$_2$), 62.99 (OCH$_2$), 125.53 (d, J=3.15 Hz), 126.11 (d, J=2.63 Hz), 129.73 (d, J=5.63 Hz), 129.96 (d, J=9.00 Hz), 133.52 (d, J=5.85 Hz), 138.42 (d, J=2.93 Hz) [aromatic carbons], 172.90 (C=O); $^{31}$P NMR (in D$_2$O) 21.53; MALDI-HRMS [M+Na]$^+$ calcd for C$_{10}$H$_{14}$NO$_5$PNa m/z 282.0507, found 282.0566; Analytical HPLC (C18-monomeric): R$_t$=6.15 min (flow rate=1 ml/min, UV 254 nm, TEAA:CH$_3$CN=95:5, gradient).

Preparation Example 9: Preparation of uridine 5'-[(2-acetylamino-5-hydroxymethyl-benzyl) phosphono]phosphate, bistriethylammonium salt (1)

The compound 10 (9.8 mg, 27.19 mmol) and 4-morpholine-N,N'-dicylcohexylcarboxamidinium uridine-5'-monophosphomorpholidate (33.70 mg, 49.08 mmol) are distilled with anhydrous pyridine under reduced pressure three times. To the residue thus obtained are added anhydrous pyridine Preparation Example 7: Preparation of diethyl-(2-acetylamino-5-acetoxymethyl-benzyl)-phosphonate (9)

The compound 8 (0.15 mg, 0.46 mmol) is dissolved in anhydrous pyridine (4 ml), and acetic anhydride (0.20 ml, 2.13 mmol) is added to the resultant solution at the room temperature. After an overnight agitation, the reactant mixture is diluted with EtOAc and neutralized with aqueous HCl (1N). The organic layer is washed with HCl (1N) twice and (0.4 ml) and 1H-tetrazole (0.1 ml, ~0.45 M in $CH_3CN$). The resultant solution is agitated at the room temperature for 7 days. The solution is treated with a few drops of water and then concentrated with toluene under reduced pressure several times. The residue thus obtained is purified by reverse-phase chromatography and RP-HPLC (C18) (triethylammonium acetate (TEAA) buffer; gradient, 010% $CH_3CN$ over 30 min) to yield the target compound 1 (13.0 mg, 60%) as a white sticky solid.

$^1H$ NMR (in $D_2O$) 1.26 (t, 18H, J=7.32 Hz, $NCH_2C\underline{H}_3$), 2.20 (s, 3H, $C=OCH_3$), 3.13-3.22 (m, 14H, $NCH_2$ and $CH_2P$), 3.94-4.24 (m, 5H, $C\underline{H}_2C\underline{H}C\underline{H}C\underline{H}$) 4.24 (s, 2H, C$\underline{H}_2OH$), 5.83 (d, 1H, J=8.15 Hz, C=OCH), 5.87 (d, 1H, J=4.74 Hz, $NCsp^3H$), 7.24 (d, 1H, J=8.05 Hz), 7.32 (s, 1H), 7.36 (d, 1H, J=7.42 Hz) [aromatic protons], 7.82 (d, 1H, J=8.12 Hz, $NCsp^2H$); $^{13}C$ NMR (in $D_2O$) 7.74 ($CH_2\underline{C}H_3$), 22.11 ($C=O\underline{C}H_3$), 31.43 (d, J=132.90 Hz, $CH_2P$), 46.18 ($NCH_2$), 62.97 ($CH_2OH$), 63.98 (d, J=5.70 Hz, $POCH_2$), 68.73, 73.27, 82.45 (d, J=9.00 Hz), 88.18 (furanose carbons), 101.97 ($C=O\underline{C}sp^2$), 125.57 (d, J=3.45 Hz), 126.10 (d, J=2.48 Hz), 129.03 (d, J=9.45 Hz), 129.89 (d, J=5.63 Hz), 133.55 (d, J=6.34 Hz), 138.33 (d, J=3.08 Hz) [aromatic carbons], 140.91 ($NCsp^2H$), 151.85 (NHC=ON), 161.59 ($Csp^2\underline{H}C=O$), 172.90 ($\underline{C}=OCH_3$); $^{31}P$ NMR (in $D_2O$) −10.01 (d, 1P, J=26.98 Hz, OPO), 14.03 (d, 1P, J=26.98 Hz, CP); MALDI-HRMS $[M+Na]^+$ calcd for $C_{19}H_{25}N_3O_{13}P_2Na$ m/z 588.0760, found 588.0779; Analytical HPLC (C18-monomeric): $R_t$=13.68 min (flow rate=1 ml/min, UV 254 nm, $TEAA:CH_3CN$=90:10, gradient).

[Experimental Example] In Vitro O-GlcNAc Transferase Inhibition Assay

FLAG-tagged human ncOGT is expressed in 293 T cells. An immunoprecipitated test is carried out using FLAG/agarose beads (Sigma, F2426), purified CKII protein (GlcNAc acceptor, BioLabs P6010, 2.2 g), ncOGT binding beads (20 1), and UDP-GlcNAc (20 M, Sigma). The O-GlcNAc inhibitor thus synthesized is added to an assay buffer (25 mM Hepes pH 7.0, 1 mM EDTA, 10 mM $MgCl_2$, 40 1) The reactant mixture is incubated at 37° C. and gently mixed every 10 minutes. After one hour, the reaction is suspended with an SDS sample buffer (0.0642 M Tris pH 6.8, 10% glycerol, 2% SDS, 0.002% BPB, 5%-mercaptoethanol). The resultant solution is centrifuged, and SDS-PAGE as the supernatant is collected. The protein is transferred from the SDS gel to a cassette containing a nitrocelluous membrane (Hybond ECL, Amersham Biosciences, RPN303D). A western blotting test is then performed using casein kinase II antibody (Santa Cruz Biotechnology, Inc. Sc-12738), 0-GlcNAc monoclonal antibody (CTD110.6, Sigma), and anti-FLAG M2 monoclonal antibody (Sigma, F3165). For visualization, West-One™ solution (iNtRON Biotechnology) is spread over the membrane, and the image is analyzed with LAS-4000 (FUJIFILM Corp.). The density of each band is calculated with Multi-gauge V3.1 program. The relative density of each band is determined by the amount of O-GlcNAc modification of CKII by ncOCT incubation. The CKII density and the FLAG bands are used as the standards for the calculation of the relative density.

According to the evaluation of effects, the compounds that belong to the chemical formula 1 have an $IC_{50}$ value of 0.1 μM to 5 mM in regards to the OGT inhibitory effect. This shows that the compounds of the chemical formula 1 can be used as an effective OGT inhibitor.

Figure 1B:
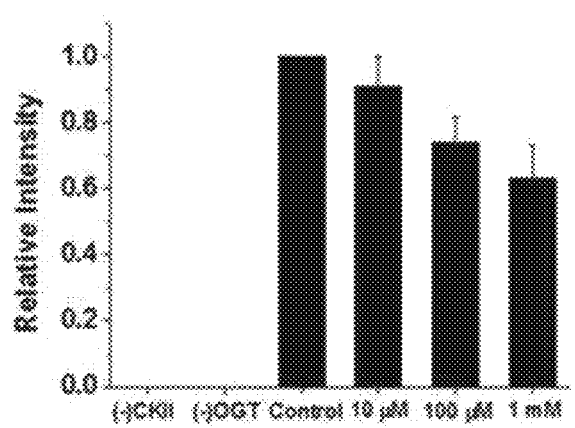

FIG. 1a presents the images showing the bands of the Western blot that represent the OGT inhibitory effect of the chemical formula 1 in the experimental example (In vitro O-GlcNAc transferase inhibition assay). FIG. 1b is a table showing the relative intensity of the anti O-GlcNAc bands of FIG. 1a.

The foregoing description of the preferred embodiments of the invention is presented for purposes of illustration and description only. It is obvious to those skilled in the art that many modifications and variations are possible in the light of the substantial characteristic of the present invention. Accordingly, the embodiments of the present invention as described in this specification are not intended to limit the scope of the present invention but to illustrate the present invention, which embodiments are not given to limit the spirit and scope of the present invention. The scope of the present invention is best defined by the appended claims and construed to include all the techniques within the equivalent scope of the present invention.

What is claimed is:
1. A compound of chemical formula 1:

[Chemical Formula 1]

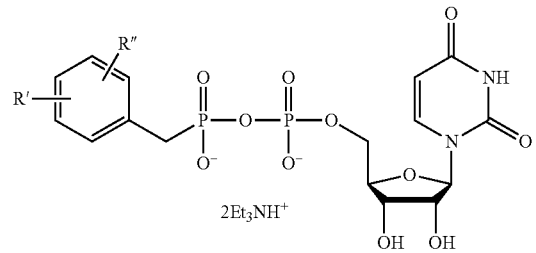

wherein R' is selected from the group consisting of —($C_1$-$C_{10}$-alkyl)-OH, —($C_1$-$C_{10}$-alkyl)-O—($C_1$-$C_6$-alkyl), —($C_1$-$C_{10}$-alkyl)-O—($C_1$-$C_6$-alkenyl), —($C_1$-$C_{10}$-alkyl)-O—($C_1$-$C_6$-alkynyl), —($C_1$-$C_6$-alkyl)-C(=O)—($C_1$-$C_6$-alkyl), —($C_1$-$C_6$-alkyl)-C(=O)—($C_1$-$C_6$-alkenyl), —($C_1$-$C_6$-alkyl)-C(=O)—($C_1$-$C_6$-alkynyl), and —($C_1$-$C_6$-alkyl)-C(=O)—O—($C_1$-$C_6$-alkyl);

R" is $NH_2$ or NHR; and

R is selected from the group consisting of —C(=O)—($C_1$-$C_{10}$-alkyl), —C(=O)—($C_1$-$C_{10}$-alkenyl), —C(=O)—($C_1$-$C_{10}$-alkynyl), —C(=O)—O—($C_1$-$C_{10}$-alkyl), —C(=O)—O—($C_1$-$C_{10}$-alkenyl), —C(=O)—O—($C_1$-$C_{10}$-alkynyl), —($C_1$-$C_{10}$-alkyl)-O—($C_1$-$C_6$-alkyl), —($C_1$-$C_{10}$-alkyl)-O—($C_1$-$C_6$-alkenyl), and —($C_1$-$C_{10}$-alkyl)-O—($C_1$-$C_{10}$-alkynyl).

2. The compound as claimed in claim 1, wherein R' is —($C_1$-$C_{10}$-alkyl)-OH, —($C_1$-$C_{10}$-alkyl)-O—($C_1$-$C_6$-alkyl), —($C_1$-$C_{10}$-alkyl)-O—($C_1$-$C_6$-alkenyl), or —($C_1$-$C_{10}$-alkyl)-O—($C_1$-$C_6$-alkenyl).

3. The compound as claimed in claim 1, wherein R' is —($C_1$-$C_{10}$-alkyl)-OH.

4. The compound as claimed in claim 1, wherein R" is NHR; and R is —C(=O)—($C_1$-$C_{10}$-alkyl), —C(=O)—($C_1$-$C_{10}$-alkenyl), or —C(=O)—($C_1$-$C_{10}$-alkynyl).

5. The compound as claimed in claim 1, wherein R" is NHR; and R is —C(=O)—($C_1$-$C_{10}$-alkyl).

6. The compound as claimed in claim 1, wherein R' is $CH_2OH$; and R" is NHAc(acetyl).

7. The compound as claimed in claim 1, wherein the compound of the chemical formula 1 has any one of the following chemical formulas 1-1 to 1-9:

<Chemical Formula 1-1>
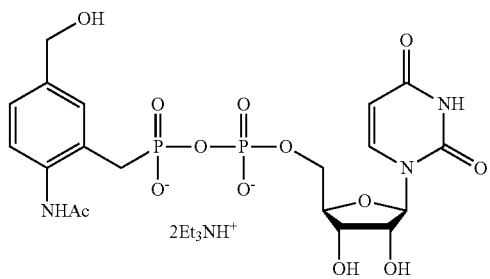
<Chemical Formula 1-2>
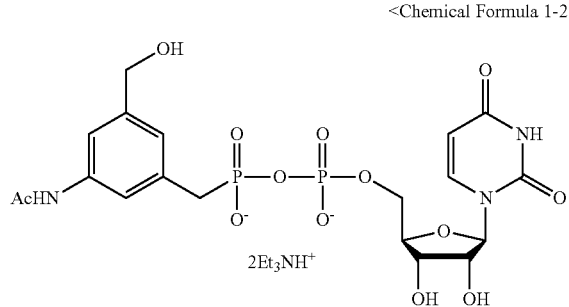
<Chemical Formula 1-3>
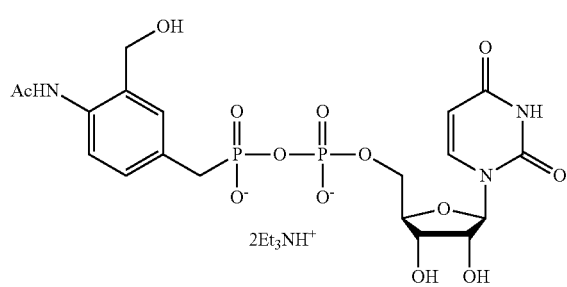
<Chemical Formula 1-4>
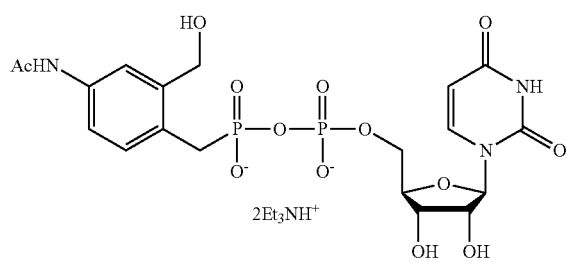
<Chemical Formula 1-5>
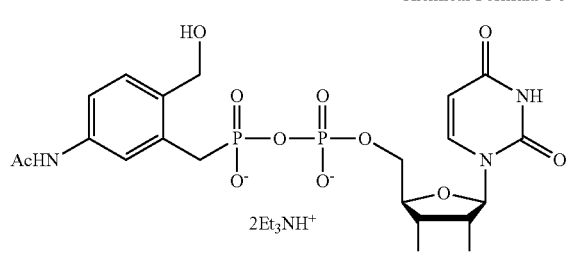
<Chemical Formula 1-6>
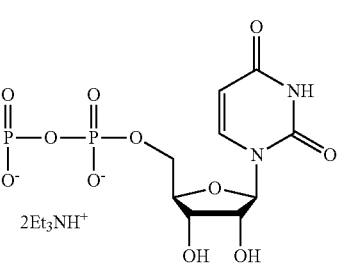
<Chmical Formula 1-7>
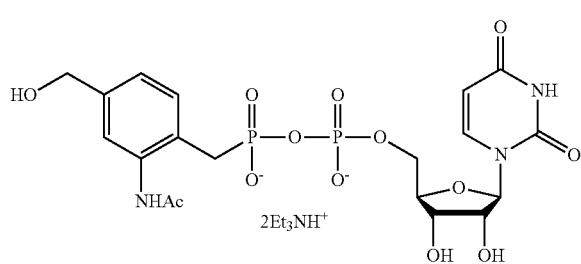
<Chemical Formula 1-8>
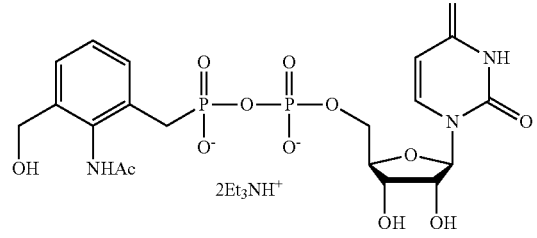
<Chemical Formula 1-9>
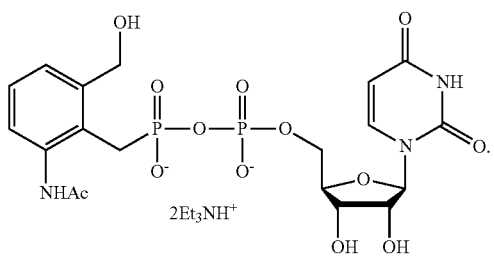
8. A method for preparing UDP-GlcNAc analogue 1:
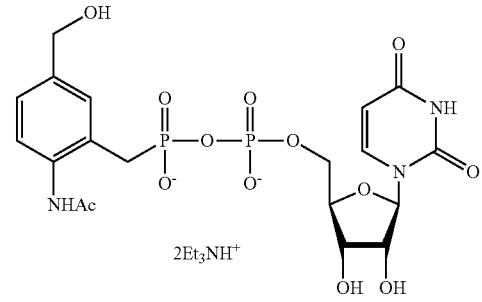
I
wherein UDP-GlcNAc analogue 1 is obtained from starting compound 2 through:

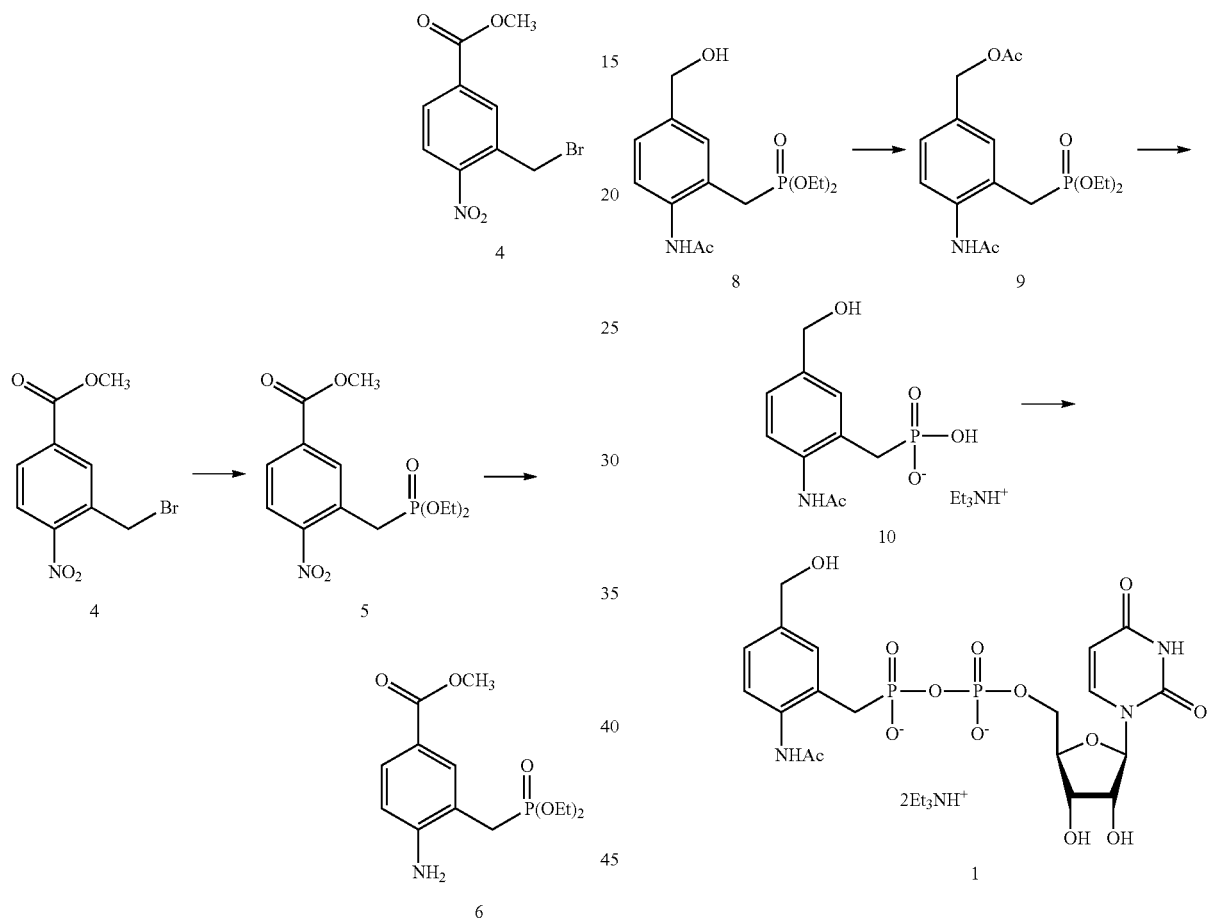

wherein
a) compound 10 and 4-morpholine-N,N'-dicylcohexylcar-boxamidinium uridine-5'-monophosphomorpholidate are distilled with anhydrous pyridine under reduced pressure;
b) to the residue thus obtained from a) is added anhydrous pyridine and 1H-tetrazole in CH$_3$CN;
c) the resultant solution from b) is agitated at the room temperature for 7 days, treated with a few drops of water, and then concentrated with toluene under reduced pressure several times; and
d) the residue thus obtained from c) is purified by reverse-phase chromatography.

* * * * *